(12) United States Patent  
Horvath

(10) Patent No.: US 9,144,582 B2
(45) Date of Patent: *Sep. 29, 2015

(54) GRANULATED MATERIAL MIXTURE COMPRISING TWO DIFFERENT GRANULATED MATERIALS FOR ARTIFICIAL CALLUS DISTRACTION

(71) Applicant: CELGEN3D AG, Zug (CH)

(72) Inventor: Domonkos Horvath, Jestetten (DE)

(73) Assignee: CELGEN3D AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/136,263

(22) Filed: Dec. 20, 2013

(65) Prior Publication Data

US 2014/0105988 A1    Apr. 17, 2014

Related U.S. Application Data

(62) Division of application No. 13/395,937, filed as application No. PCT/EP2010/005600 on Sep. 13, 2010, now Pat. No. 8,617,612.

(30) Foreign Application Priority Data

Sep. 14, 2009   (DE) .................... 10 2009 042 493

(51) Int. Cl.
| | |
|---|---|
| *A61K 9/50* | (2006.01) |
| *A61K 33/42* | (2006.01) |
| *A61K 9/16* | (2006.01) |
| *A61L 27/12* | (2006.01) |
| *A61L 27/20* | (2006.01) |
| *A61L 27/42* | (2006.01) |

(Continued)

(52) U.S. Cl.
CPC ............... *A61K 33/42* (2013.01); *A61K 9/1623* (2013.01); *A61K 9/1652* (2013.01); *A61L 27/12* (2013.01); *A61L 27/20* (2013.01); *A61L 27/425* (2013.01); *A61L 27/46* (2013.01); *A61L 27/50* (2013.01); *A61L 2430/02* (2013.01)

(58) Field of Classification Search
CPC ......................... A61K 9/1623; A61K 9/1652
See application file for complete search history.

(56) References Cited

U.S. PATENT DOCUMENTS

2002/0169506 A1   11/2002   Matsushima et al.
2009/0028954 A1   1/2009    Bohner et al.

FOREIGN PATENT DOCUMENTS

| DE | 19706667 A1 | 8/1998 |
|---|---|---|
| DE | 10258773 A1 | 7/2004 |
| DE | 102005034420 A1 | 7/2006 |

(Continued)

OTHER PUBLICATIONS

International Search Report for PCT/EP2010/005600, ISA/EP, Rijswijk, NL, mailed May 17, 2011.

(Continued)

*Primary Examiner* — Carlos Azpuru
(74) *Attorney, Agent, or Firm* — Harness, Dickey & Pierce, P.L.C.

(57) ABSTRACT

A granulate mixture suitable for regenerating a bone contains at least one expandable particle and at least one nondeformable particle. The at least one expandable particle contains a swelling agent. The swelling is enclosed by a biodegradable sheathing or be a biodegradable casing. Three-dimensional callus distraction may be accomplished by introducing the granulated mixture into a bone defect.

19 Claims, 2 Drawing Sheets

(51) Int. Cl.
*A61L 27/46* (2006.01)
*A61L 27/50* (2006.01)

(56) References Cited

FOREIGN PATENT DOCUMENTS

| DE | 102006042142 A1 | 3/2008 |
|---|---|---|
| DE | 102007050440 A1 | 4/2009 |
| DE | 102008014560 A1 | 9/2009 |
| DE | 102008064628 A1 | 9/2009 |
| WO | 03/082365 A1 | 10/2003 |
| WO | 2008/077257 * | 7/2008 |
| WO | 2008/077257 A1 | 7/2008 |

OTHER PUBLICATIONS

International Preliminary Report on Patentability (Chapter II) with annexes (15 pages), IPEA/EP, issued Oct. 20, 2011.

* cited by examiner

GRANULATED MATERIAL MIXTURE COMPRISING TWO DIFFERENT GRANULATED MATERIALS FOR ARTIFICIAL CALLUS DISTRACTION

CROSS-REFERENCE TO RELATED APPLICATIONS

This application is a divisional of U.S. patent application Ser. No. 13/395,937 filed on 14 Mar. 2012, which is a 371 U.S. National Stage of International Application No. PCT/EP2010/005600, filed Sep. 13, 2010, which claims priority to German Patent Application No. 10 2009 042 493.8, filed Sep. 14, 2009. The entire disclosures of the above applications are incorporated herein by reference.

FIELD

The present invention relates to a granulate mixture for regenerating a bone, in particular by means of three-dimensional distraction, methods for three-dimensional callus distraction, and uses of said granulate mixture.

BACKGROUND

This section provides background information related to the present disclosure which is not necessarily prior art.

At the present time, bone losses are generally filled using bone replacement materials, or autogenic or allogic bone.

Examples of bone replacement materials include inorganic materials such as calcium phosphate, hydroxyapatite, or bioglass, which are replaced by bone after a long absorption period. However, this procedure may be used only for minor defects; otherwise, there is the risk of infection due to insufficient vascularization. Such bone materials do not emit biomechanical pulses and therefore do not initiate active regeneration. There are also synthetically manufactured bone replacement materials made of organic materials, such as polyesters, polyamino acids, polyanhydrides, polyorthoesters, polyphosphazenes, polylactides, or polyglycolides, or made of allogenic organic materials, for example of bovine origin. However, bone substance losses may also be compensated for using microvascular connected autogenic or allogenenically vascularized transplants.

From a biological standpoint, the best replacement material for bone is an autologous spongiosa transplant. However, such transplants have limited availability and exhibit a high absorption rate after transplantation.

The materials and techniques used in the prior art frequently provide unsatisfactory bone quality, resulting, for example, in insecure anchoring of implant beds. In addition, frequently the bone replacement is insufficiently vascularized, thereby increasing the risk of infection. Furthermore, methods of the prior art often use growth factors which greatly increase the costs for the methods.

Bone replacement materials are frequently used in the form of a granulated material, in particular in the mouth and jaw region. Such a granulated material is described in WO 2006/010507 A2, for example. Examples of granulated material known on the market include Bio-Oss® from Geistlich Pharma AG, BONITmatrix® from DOT GmbH, and cycIOS® and Ceros® from Mathys AG.

Instead of using a bone replacement, missing bone substance may sometimes be filled by bone regeneration. Segmented interruptions in the osseous continuity of long tubular bones may be treated in this manner by distraction osteogenesis.

Callus distraction has been known for over a hundred years. The most important biological stimulus for bone formation is mechanical stress. This releases piezoelectric forces which activate the osteoblasts and osteoclasts. Distraction osteogenesis induces new bone formation by triggering biological growth stimuli by means of slow separation of bone segments. This method achieves direct formation of woven bone by distraction. The defined tensile stress is essential for bone formation. When such a defined tensile stress is applied to bone fragments, the mesenchymal tissue exhibits an osteogenetic potential in the gap and at the contiguous fragment ends. When sufficient vascular potency is present, progressive distraction results in metaplasia of the organized hematoma, also referred to as blood coagulum, in a zone of longitudinally arranged fibrous tissue, which under optimal external and internal conditions may be directly converted to woven bone. A complication, however, is that the bone tissue requires highly complex control for regeneration.

WO 01/91663 describes a two-dimensionally oriented bone distraction using an artificial interface. For such distraction methods from the prior art, in many cases only vertical regeneration is possible, for example in the jaw region.

Thus, bone regeneration by distraction cannot be used for every type of bone defect. In addition, the devices used for distraction are complex, and distraction methods take a comparatively long time.

DE 10 2006 047 248 A1 describes a three-dimensional structure which, by a change in volume, transmits pulses directly to osteoblasts and activates same.

SUMMARY

This section provides a general summary of the disclosure, and is not a comprehensive disclosure of its full scope or all of its features.

The technical object of the present invention is to provide a device which allows bone regeneration methods to be carried out which overcome the disadvantages of the prior art. A further technical object of the invention is the provision of devices which improve the previously known devices for bone regeneration, in particular in a simple manner.

A further technical object of the invention is the provision of devices, use of same, and methods which allow simple and economical bone regeneration.

A further technical object of the invention is the provision of devices, use of same, and methods which allow regeneration of bone and which have improved quality and sufficient vascularization.

The technical object is achieved by the present invention in particular by providing devices, methods, and uses according to the claims.

The devices according to the invention are in particular granulate mixtures according to the invention.

The technical object is achieved by the present invention in particular by providing a granulate mixture which is suitable for regenerating a bone, and which contains at least one deformable particle and at least one nondeformable particle.

The technical object is further achieved by the present invention in particular by providing a granulate mixture which is suitable for regenerating a bone, and which contains at least one expandable particle and at least one nonexpandable particle.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
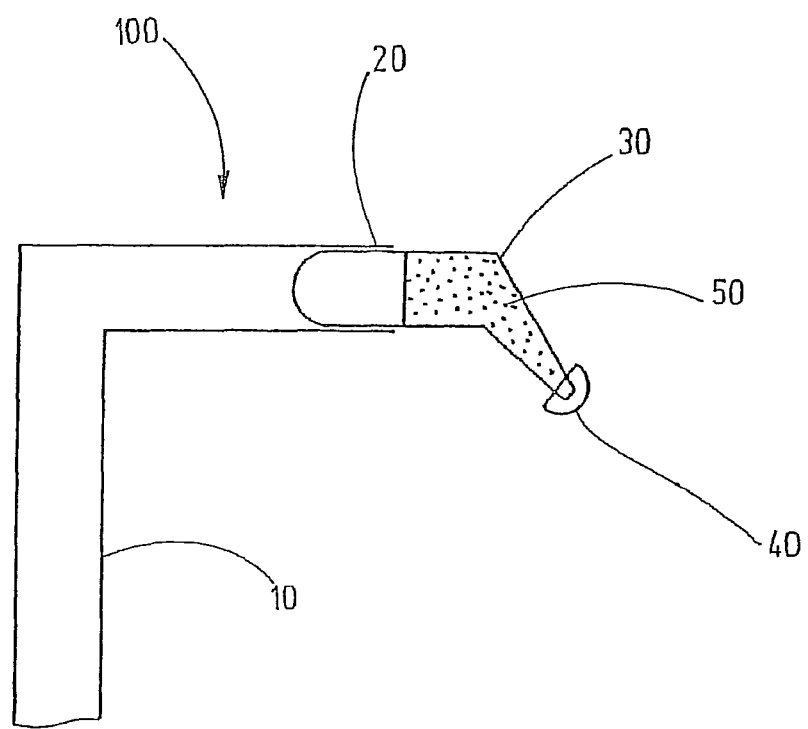
FIG. 1 is an environmental view illustrating a granulate mixture in accordance with the present teachings incorporated into a disposable capsule and shown operatively associated with a syringe.

Corresponding reference numerals indicate corresponding parts throughout the several views of the drawings.

According to the invention, the granulate mixture preferably contains a plurality of the deformable particles and a plurality of the nondeformable particles.

According to the invention, the granulate mixture preferably contains a plurality of the expandable particles and a plurality of the nonexpandable particles.

According to the invention, in one alternative embodiment it may be provided that the granulate mixture is composed of at least one deformable particle and at least one nondeformable particle.

The granulate mixture according to the invention may be advantageously used in methods, preferably methods according to the invention, for bone regeneration, in particular for three-dimensional callus distraction.

The present teaching encompasses in particular granulate mixtures and methods for bone regeneration, wherein preferably bone in the jaw region and/or periodontal region is to be regenerated.

In particular, for the present invention the term "bone regeneration" is also understood to mean the regeneration of bone defects, for example after cystectomy, tumor surgery, or trauma surgery, etc., regardless of the topography, and/or in particular also means the regeneration of minor bone defects, for example those caused by periodontitis.

However, bone outside the jaw region and/or outside the periodontal region may also be regenerated.

According to the invention, preferably any mixing ratio of the deformable particles to the nondeformable particles in the granulate mixture may be provided, as needed.

According to the invention, preferably any mixing ratio of the expandable particles to the nonexpandable particles in the granulate mixture may be provided, as needed.

According to the invention, the mixing ratio of the deformable particles to the nondeformable particles in the granulate mixture is preferably 1:999 to 999:1, relative to the number of particles. According to the invention, the mixing ratio of the deformable particles to the nondeformable particles in the granulate mixture is preferably 1:99 to 99:1, relative to the number of particles.

It may be provided, for example, that the mixing ratio of the deformable particles to the nondeformable particles in the granulate mixture is 1:9 to 9:1, relative to the number of particles.

According to the invention, the mixing ratio of the expandable particles to the nonexpandable particles in the granulate mixture is preferably 1:999 to 999:1, relative to the number of particles. According to the invention, the mixing ratio of the expandable particles to the nonexpandable particles in the granulate mixture is preferably 1:99 to 99:1, relative to the number of particles.

It may be provided, for example, that the mixing ratio of the expandable particles to the nonexpandable particles in the granulate mixture is 1:9 to 9:1, relative to the number of particles.

In one alternative embodiment it may be provided, for example, that more nondeformable particles are present in the granulate mixture than deformable, in particular expandable, particles.

According to the invention, the at least one deformable particle preferably contains a swelling agent. It may be provided, for example, that the at least one deformable particle is composed of a swelling agent.

According to the invention, the at least one expandable particle preferably contains a swelling agent. It may be provided, for example, that the at least one expandable particle is composed of a swelling agent.

In one alternative according to the invention, the swelling agent may be solid. In one alternative according to the invention, the swelling agent may be semisolid. In one alternative according to the invention, the swelling agent may be present as a foam. In one alternative according to the invention, the swelling agent may be present as a powder, in particular when the swelling agent is enclosed by a casing or sheathing. In one alternative according to the invention, the swelling agent may be present as a liquid, in particular when the swelling agent is enclosed by a sheathing.

In one alternative according to the invention, the expandable particle may be solid. In one alternative according to the invention, the expandable particle may be semisolid. In one alternative according to the invention, the expandable particle may be present as a foam. The expandable particle may be present in particular as a solid, semisolid, or foam when the expandable particle is composed of a swelling agent.

According to the invention, the swelling agent is preferably biocompatible. According to the invention, the swelling agent is preferably biodegradable.

It may be provided, for example, that the swelling agent is not biogenic, in particular that the swelling agent contains no collagen or is collagen-free. However, it may also be provided that the swelling agent is biogenic.

However, it may also be provided, for example, that the swelling agent of the at least one deformable, in particular expandable, particle is enclosed by a biodegradable casing. The casing may be formed from one or multiple biodegradable materials. The undegraded, i.e., intact, casing prevents contact of the swelling agent with a liquid. The swelling agent may come into contact with a liquid after the casing has partially or completely degraded.

By selecting the thickness of the casing, one skilled in the art may specify the period of time over which the shell dissolves. It is thus possible to predefine the point in time that distraction begins. The thicker the biodegradable casing, for example, the later the onset of deformation, in particular expansion, of the encased granulated material, and thus, the start of the distraction pulses.

The thickness of the casing may be from the thickness of a molecular film up to 5 mm. According to the invention, the casing preferably has at least the thickness of a molecular film. According to the invention, the casing preferably has a maximum thickness of 5 mm, in particular 2 mm, very particularly very 1 mm. In one embodiment according to the invention, the casing has a thickness between 0.1 μm and 1 mm. In one embodiment according to the invention, the casing has a thickness of at least 10 μm and a maximum of 100 μm.

In one embodiment according to the invention, the casing may have an absorption time of at least one day, for example. In one embodiment according to the invention, the casing may have an absorption time of at least five days, for example. In one embodiment according to the invention, the casing may have an absorption time of approximately one week, for example. In one embodiment according to the invention, the casing may have an absorption time of 4 days to 10 days, for example. In one embodiment according to the invention, the casing may have an absorption time of 6 days to 8 days, for example. In one embodiment according to the invention, the casing may have an absorption time of 10 weeks maximum, in particular 3 weeks maximum, for example. In one embodiment according to the invention, the casing may have an absorption time of at least one day and a maximum of ten weeks, for example. In one embodiment according to the invention, the casing may have an absorption time of at least one day and a maximum of one week, for example. In one embodiment according to the invention, the casing may have an absorption time of at least one week and a maximum of ten weeks, for example.

In one embodiment according to the invention, the casing may, for example, be composed of gelatin or contain gelatin. In one embodiment according to the invention, the casing may, for example, be composed of substances or contain same which are gelatin-like or which have the properties of gelatin. Such substances are known to one skilled in the art, in particular from the field of galenics.

The use of gelatin or gelatin-like substances has the advantage that the degradation of the gelatin does not lower the pH of the surroundings, since no acidic degradation products arise.

In one embodiment according to the invention, the casing may be composed of at least one gelatin film, for example.

However, it may also be provided, for example, that the swelling agent of the at least one deformable, in particular expandable, particle is enclosed by a biodegradable sheathing. According to the invention, the swelling agent is preferably located inside the sheathing, i.e., is surrounded by the sheathing. According to the invention, the sheathing thus preferably forms a cavity in which the swelling agent is present. According to the invention, a portion of the cavity, in particular the entire cavity, which is formed by the sheathing is preferably filled with the swelling agent. According to the invention, preferably the entire cavity which is formed by the sheathing is filled with the swelling agent. The cavity is delimited by the sheathing, even when the sheathing has openings, for example pores.

According to the invention, the sheathing preferably reacts to the change in volume of the swelling agent by expansion, deformation, and/or contraction. According to the invention, the sheathing preferably reacts to the change in volume of the swelling agent by expansion. According to the invention, the sheathing preferably reacts to the change in volume of the swelling agent by deformation. According to the invention, the sheathing preferably reacts to the change in volume of the swelling agent by expansion and deformation.

According to the invention, the sheathing preferably contains a material selected from the group comprising polyglycolic acid, polylactic acid, poly(ε-caprolactone), poly(β-hydroxybutyrate), poly(p-dioxanone), a polyanhydride, or a mixture of same, for example a mixture of polylactic acid and polyglycolic acid. According to the invention the sheathing preferably contains polylactic acid. According to the invention the sheathing preferably contains poly(ε-caprolactone). According to the invention the sheathing preferably contains a carbolactone.

According to the invention, the material of the sheathing preferably contains copolymers, in particular composed of at least two of the above-mentioned materials. According to the invention, the material of the sheathing preferably contains polymer mixtures.

According to the invention, the sheathing is preferably composed of a material selected from the group comprising polyglycolic acid, polylactic acid, poly(ε-caprolactone), poly(β-hydroxybutyrate), poly(p-dioxanone), a polyanhydride, or a mixture of same. According to the invention, the material of the sheathing is preferably composed of copolymers of at least two of the above-mentioned materials.

According to the invention the sheathing is preferably composed of polylactic acid. Sheathing which contains or is composed of polylactic acid has the advantage that the polylactic acid is degraded into short-chain metabolites. In addition, polylactic acid imparts a certain hardness to the sheathing.

According to the invention the sheathing is preferably composed of poly(ε-caprolactone). Sheathing which contains or is composed of poly(ε-caprolactone) has the advantage that poly(ε-caprolactone) is particularly biocompatible. In addition, long chains composed of poly(ε-caprolactone) may be formed. Little or no free acids are formed from poly(ε-caprolactone) during decomposition.

According to the invention the sheathing is preferably composed of carbolactone.

According to the invention the sheathing is preferably composed of or contains at least one polymer, preferably a polymer composed of spatially crosslinked polymers.

According to the invention, the material of the sheathing is particularly preferably composed of at least one fiber composite or contains same. According to the invention, the material of the sheathing is particularly preferably composed of fibers of a fiber composite or contains same.

In one embodiment according to the invention, the sheathing is composed of gelatin or gelatin-like substances, or contains same.

According to the invention the sheathing preferably has at least one cell adhesive property; i.e., it is able to bind cells, in particular osteoblasts, fibroblasts, and/or endothelial cells, and preferably is able to bind specifically and selectively. According to the invention, the cell adhesive property of the sheathing is preferably determined by its surface characteristics.

According to the invention, before introduction into a defect region of a bone the sheathing is preferably externally coated with cells, in particular endothelial cells and/or osteoblasts and/or fibroblasts.

According to the invention the material of the sheathing is preferably smooth. According to the invention the coating of the sheathing is preferably smooth. According to the invention the material of the sheathing is preferably rough. According to the invention the coating of the sheathing is preferably rough. A larger surface is available for binding of the osteoblasts by use of a preferred rough surface according to the invention.

According to the invention the sheathing is preferably coated with hydroxyapatite. A coating with hydroxyapatite preferred according to the invention allows adsorption of proteins, which promotes binding.

According to the invention the sheathing is preferably coated with a hydrogel. According to the invention the hydrogel layer is preferably thin.

According to the invention the sheathing is preferably coated with at least one protein. According to the invention the at least one protein preferably contains the amino acid sequence Arg-Gly-Asp, i.e., RGD. According to the invention the sheathing is preferably coated with at least one peptide. According to the invention the at least one peptide is preferably a peptide which initiates the cell adhesion. According to the invention the at least one peptide is preferably an RGD peptide. According to the invention the at least one peptide is preferably synthetically produced. According to the invention the at least one peptide preferably contains the amino acid sequence Arg-Gly-Asp, i.e., RGD. According to the invention the at least one peptide preferably comprises the amino acid sequence Arg-Gly-Asp, i.e., RGD.

According to the invention the sheathing is preferably coated with star-shaped polyethylene glycol polymers (star PEG).

According to the invention, the at least one protein is preferably bound, particularly preferably covalently bound, to the polyethylene glycol polymer coating. According to the invention, the at least one peptide is preferably bound, particularly preferably covalently bound, to the polyethylene glycol polymer coating.

The adhesion of osteoblasts is a receptor-mediated contact between the molecules of the extracellular matrix and the actin fibers of the cytoskeleton. This region is also referred to as the focal contact zone. Molecules which provide for binding as well as molecules which are responsible for signal transduction are present in the focal contacts. Formation of the focal adhesion is caused primarily by integrins. The integrins differ from other cell surface receptors by virtue of their bioaffinity. Adhesion proteins in the form of an ultrathin coating on the sheathing facilitate the adhesion binding of osteoblasts to the device according to the invention. Fibronectin is an extracellular adhesion protein having multiple specific binding sites for receptors, and is therefore used for binding the osteoblasts to the extracellular matrix. Fibronectin is a large glycoprotein, which as a dimer is composed of two essentially identical subunits. Fibronectin is composed of approximately 90 amino acids. The cell-binding site of fibronectin has been identified as the tripeptide sequence Arg-Gly-Asp (RGD).

According to the invention, the surface of the sheathing is preferably chemically modified. According to the invention, the surface of the sheathing is preferably chemically modified by reactive molecules or groups of molecules. According to the invention, the molecules or groups of molecules by means of which the surface of the sheathing is chemically modified are preferably able to react with anchor proteins of the extracellular matrix of cells. According to the invention the surface of the sheathing is preferably hydrophilic. Hydrophilic surfaces allow better adhesion for cells than do hydrophobic surfaces.

According to the invention the sheathing preferably has a thickness of at least 0.01 mm. According to the invention the sheathing preferably has a maximum thickness of 1 mm. According to the invention the sheathing preferably has a thickness of at least 0.05 mm and a maximum thickness of 0.5 mm. According to the invention the sheathing preferably has a thickness of approximately 0.1 mm.

According to the invention the sheathing is preferably permeable to a liquid. According to the invention the sheathing is preferably permeable to water. According to the invention the sheathing is preferably porous. According to the invention the sheathing preferably has pores which are permeable to water and to solids, for example proteins and sugars having a mass of less than 100 kDa, particularly preferably less than 50 kDa. According to the invention the sheathing preferably has pores which are nonpermeable to solids, for example proteins and sugars having a mass of greater than 50 kDa, particularly preferably greater than 100 kDa, in particular greater than 150 kDa. According to the invention, the pores preferably have a size of 2 μm maximum, particularly preferably 1 μm maximum. According to the invention, the pores preferably have a size of 0.5 μm maximum, particularly preferably 0.1 μm maximum. According to the invention, the pores preferably have a size of at least 0.01 μm, particularly preferably at least 0.05 μm. According to the invention, the pores preferably have a size of at least 0.1 μm, particularly preferably at least 0.5 μm. According to the invention, the pores preferably have a size of 1 μm.

According to the invention, at least a part of the sheathing preferably has the shape of a bellows.

According to the invention, at least a part of the sheathing preferably has the shape of a corrugated hose.

According to the invention, the sheathing preferably has the shape of a bellows.

According to the invention, the sheathing preferably has the shape of a corrugated hose.

The part of the sheathing shaped as a bellows or corrugated hose may be pulled apart or pushed together in the same way as for the similar part of a flexible drinking straw.

The bellows or corrugated hose is preferably composed of at least one, particularly preferably at least two, in particular a plurality of folds.

According to the invention, the folds of the bellows or corrugated hose preferably have a length of 0.5 mm to 2 mm, calculated from the inner circumference of the sheathing to the distal end of the folds, which in a manner of speaking form the outer circumference. According to the invention, the folds of the bellows or corrugated hose preferably have a length of 1 mm.

According to the invention, the at least one part of the sheathing shaped as a bellows or corrugated hose is preferably pushed together in the initial state, i.e., before use of the particles. The preferably at least one part of the sheathing shaped as a bellows or corrugated hose is pushed apart as a result of the change in volume, in particular the increase in volume, of the swelling agent.

According to the invention the outer surface of the sheathing is enlarged, in particular as the result of providing contours. This enlargement not only increases the surface that is available to the cells, but also influences the organization of cellular growth.

According to the invention, the outer surface of the sheathing is preferably enlarged by means of lamellae. In one preferred embodiment of the present invention the lamellae have rod- or tube-like projections. In another particularly preferred embodiment the lamellae have planar projections, in particular wall-, plate-, leaf-, fan-, or wing-like or other planar projections. In a further preferred embodiment the lamellae have enlarged surfaces, in particular as the result of lamellae substructures, branches, protuberances, or meshlike structures.

According to the invention the exterior of the sheathing preferably bears at least one lamella. According to the invention the exterior of the sheathing preferably bears at least two lamellae. According to the invention the exterior of the sheathing preferably bears a plurality of lamellae. According to the invention the exterior of the sheathing preferably bears 2 to 20 lamellae.

According to the invention, the at least one lamella may preferably be a component of the sheathing. According to the invention, the at least one lamella is preferably composed of the same material as the sheathing.

According to the invention, the at least one lamella is preferably not a component of the sheathing. According to the invention, the at least one lamella is preferably composed of a different material than the sheathing.

According to the invention the sheathing is preferably biocompatible. According to the invention the sheathing is preferably biodegradable. According to the invention the sheathing and/or the swelling agent is/are preferably biodegradable.

In the context of the present invention, "biodegradable" is understood to mean that the material may be degraded or absorbed by hydrolysis, polymer degradation, enzymatic decomposition, and/or dissociation of the material components, preferably in an organism, for example a human or animal organism. According to the invention, the degradation products of the particles preferably have a molecular weight of 50,000 g/mol maximum, particularly preferably 40,000 g/mol maximum. Thus, they may be excreted in the normal manner.

According to the invention, the biodegradable, deformable particles are preferably degraded in an organism within an absorption time of two years, particularly preferably within one year, in particular within one month, most preferably within two weeks.

According to the invention, the absorption preferably begins 6 weeks after the particles are introduced into an organism.

According to the invention, the absorption time for the biodegradable, deformable particles, in particular of the sheathing and/or of the swelling agent, is at least 4 weeks, particularly preferably at least 8 weeks, in particular at least 16 weeks, most preferably at least 32 weeks. According to the invention, the absorption time for the biodegradable, deformable particles is preferably a maximum of 52 weeks, particularly preferably a maximum of 38 weeks, more preferably a maximum of 16 weeks, most preferably a maximum of 8 weeks.

According to the invention, the biodegradable, deformable particles are preferably biodegradable. According to the invention, the components of the device, in particular the sheathing and the swelling agent, are preferably biodegradable.

In one alternative embodiment according to the invention, the deformable, in particular expandable, particles have no sheathing.

In one alternative embodiment according to the invention, the deformable, in particular expandable, particles have no casing.

In one alternative embodiment according to the invention, the deformable, in particular expandable, particles are porous. In one alternative embodiment according to the invention, the deformable, in particular expandable, particles are nonporous.

In one embodiment it may be provided that the swelling agent is a hydrogel.

According to the invention the hydrogel is preferably carboxymethylcellulose. According to the invention the hydrogel preferably contains carboxymethylcellulose. According to the invention the hydrogel is preferably composed of a polysaccharide. According to the invention the hydrogel preferably contains at least one polysaccharide. According to the invention the hydrogel is preferably hyaluronic acid. According to the invention the hydrogel preferably contains hyaluronic acid. According to the invention the swelling agent preferably contains various components, in particular mixtures of the components disclosed herein, such as carboxymethylcellulose, polysaccharides, and/or hyaluronic acid.

In one embodiment according to the invention, the hydrogel may be polyethylene glycol (PEG). In one embodiment according to the invention, the hydrogel may contain polyethylene glycol (PEG). In one embodiment according to the invention, the hydrogel may be polyacrylamide. In one embodiment according to the invention, the hydrogel may contain polyacrylamide.

In one embodiment, it may be provided in particular that the swelling agent of the at least one deformable, in particular expandable, particle is composed of a polysaccharide.

In one embodiment, it may be provided in particular that the swelling agent of the at least one deformable, in particular expandable, particle is composed of a glucosamine.

In one embodiment, it may be provided in particular that the plurality of the deformable, in particular expandable, particles is composed of the same or of different materials.

According to the invention, the deformation, in particular the expansion, of the swelling agent as a result of the absorption of liquid, preferably a liquid containing biomolecules and/or cells, particularly preferably blood, is preferably induced by the swelling agent.

According to the invention, the least one deformable particle preferably has a particle size of 0.1 µm to 10 mm.

According to the invention, the at least one expandable particle preferably has a particle size of 0.1 µm to 10 mm.

In one alternative embodiment according to the invention, the at least one deformable particle has a particle size of 0.1 mm to 10 mm.

In one alternative embodiment according to the invention, the at least one expandable particle has a particle size of 0.1 mm to 10 mm.

In one alternative embodiment according to the invention, the at least one deformable particle has a particle size of at least 0.1 µm. In one alternative embodiment according to the invention, the at least one deformable particle has a particle size of at least 1 µm. In one alternative embodiment according to the invention, the at least one deformable particle has a particle size of at least 10 µm. In one alternative embodiment according to the invention, the at least one deformable particle has a particle size of at least 100 µm. In one alternative embodiment according to the invention, the at least one deformable particle has a particle size of at least 200 µm.

In one alternative embodiment according to the invention, the at least one deformable particle has a maximum particle size of 10 mm. In one alternative embodiment according to the invention, the at least one deformable particle has a maximum particle size of 5 mm. In one alternative embodiment according to the invention, the at least one deformable particle has a maximum particle size of 1 mm.

In one preferred embodiment, the particle size of the deformable particles and of the nondeformable particles is at least 0.0001 mm. In one preferred embodiment, the particle size of the deformable particles and of the nondeformable particles is at least 0.001 mm. In one preferred embodiment, the particle size of the deformable particles and of the nondeformable particles is at least 0.01 mm.

In one preferred embodiment, the deformable and/or the nondeformable particles are in the form of a granulate, not a powder. In one preferred embodiment, the deformable particles and the nondeformable particles are in the form of a granulate, not a powder.

In one embodiment according to the invention, the particle size is 0.2 mm to 5 mm. In one embodiment according to the invention, the particle size is 0.5 mm to 5 mm. In one embodiment according to the invention, the particle size is 0.6 mm to 5 mm. In one embodiment according to the invention, the particle size is 0.5 mm to 4 mm.

In one preferred embodiment, the particle size is at least 0.001 mm. In one preferred embodiment, the particle size is at least 0.01 mm.

In one embodiment according to the invention, the particle size is at least 0.0001 mm. In one embodiment according to the invention, the particle size is at least 0.1 mm. In one embodiment according to the invention, the particle size is at least 0.2 mm. In one embodiment according to the invention, the particle size is at least 0.3 mm. In one embodiment according to the invention, the particle size is at least 0.4 mm. In one embodiment according to the invention, the particle size is at least 0.5 mm. In one embodiment according to the invention, the particle size is at least 0.6 mm.

In one embodiment according to the invention, the maximum particle size is 10 mm. In one embodiment according to the invention, the maximum particle size is 5 mm. In one embodiment according to the invention, the maximum particle size is 4 mm. In one embodiment according to the invention, the maximum particle size is 2 mm. In one embodiment according to the invention, the maximum particle size is 1 mm.

The information concerning the particle sizes of the deformable, in particular expandable, particles relates to the size of the particles in the starting state, i.e., in the undeformed or unexpanded state.

In one alternative embodiment, it may be provided in particular that the particles of the plurality of the deformable, in particular expandable, particles are present in a single particle size.

However, in one alternative embodiment it may also be provided that the particles of the plurality of the deformable, in particular expandable, particles are present in at least two different particle sizes. In one alternative embodiment, it may also be provided in particular that the particles of the plurality of the deformable, in particular expandable, particles are present in two different particle sizes. In one alternative embodiment, it may also be provided in particular that the particles of the plurality of the deformable, in particular expandable, particles are present in three different particle sizes. In one alternative embodiment, it may also be provided in particular that the particles of the plurality of the deformable, in particular expandable, particles are present in four different particle sizes. In one alternative embodiment, it may also be provided in particular that the particles of the plurality of the deformable, in particular expandable, particles are present in five different particle sizes.

In one alternative embodiment, it may also be provided in particular that the particles of the plurality of the deformable, in particular expandable, particles of the granulate mixture are present one to ten, in particular one to five, or also in two to ten, in particular two to five, different particle sizes.

In one alternative embodiment, it may also be provided in particular that the particles of the plurality of the deformable, in particular expandable, particles of the granulate mixture are present in a plurality of different particle sizes.

According to the invention, the at least one deformable particle is preferably expandable or contractible and/or is able to change its shape in some other way, for example by changing the surface contour. According to the invention, the at least one deformable particle is preferably expandable and/or contractible. According to the invention, the at least one deformable particle is preferably expandable or contractible.

According to the invention, the at least one deformable particle is preferably expandable.

According to the invention, the deformable particles are preferably expandable particles.

According to the invention, the deformable particles are preferably expandable in a predefined and controlled manner as a function of the action of force. According to the invention, the deformable particles are preferably deformable in a predefined and controlled manner as a function of the action of force.

According to the invention, the at least one deformable particle is preferably contractible.

According to the invention, the deformation of the at least one deformable particle preferably occurs as the result of a change in volume of the particle.

In the context of the present invention, the "volume" of the deformable particles and in particular of the swelling agent is understood to mean the volume that is delimited by the outer surfaces of the particles or of the swelling agent. The deformable particles are preferably present in the form of a starting volume, preferably the original starting volume, which is able to change to a different volume as the result of contact with a liquid, in particular as the result of absorption of liquid. A change in the volume means a change in the starting volume, in particular a significant change in the starting volume, preferably an increase in the starting volume. The change may be, for example, a change in the starting volume of at least 1%, preferably 5%, preferably 10%, preferably 15%, preferably 20%, preferably 30%, preferably 40%, preferably 50%, preferably 60%, preferably 70%, preferably 80%, preferably 90%, and in the case of an enlargement, preferably at least 100%, preferably 150%, preferably 200%, or preferably 300%, for example as the result of expansion or deformation of the particles.

In one embodiment according to the invention, the deformation, in particular expansion, of a deformable particle takes place in all three spatial directions. In one alternative embodiment according to the invention, the deformation, in particular expansion, takes place directed in one or two spatial directions. In one alternative embodiment according to the invention, the deformation, in particular expansion, takes place directed in one spatial direction. A directed deformation, in particular expansion, may be achieved, for example, by a sheathing, in particular a sheathing having a bellows. However, the directed expansion may also be achieved, for example, by a casing having different thicknesses at different locations, and which therefore dissolves at different rates. In that case, a deformation, in particular expansion, takes place at regions of the swelling agent at which the casing is already dissolved, and not at locations at which the casing has not yet dissolved.

According to the invention, the change in volume of the deformable particles as a result of contact with and absorption of liquid, preferably a liquid containing biomolecules and/or cells, particularly preferably blood, is preferably induced by the particles, for example by the swelling agent. According to the invention the liquid is preferably water. According to the invention the liquid is preferably a bodily fluid. According to the invention the liquid is preferably an interstitial liquid. According to the invention the liquid is preferably blood. According to the invention, the absorbed liquid preferably contains no solid constituents larger than 150 kDa, particularly preferably larger than 100 kDa, in particular larger than 50 kDa.

According to the invention, the change in volume of the deformable particles is preferably an increase in volume.

Provision of the granulate mixture according to the invention allows the granulate mixture to be introduced into a bone defect, for example by surgical means. After introduction into the bone defect, according to the invention the volume of the deformable particles changes, for example increases or decreases, but in particular expands, due to contact with a liquid and associated liquid migration, in particular absorption of the liquid. As a result of the change in volume of the deformable particles, the deformable particles are changed in shape and/or size, particularly preferably the surface and thus the enclosed volume being enlarged. As a result, after introduction of the granulate mixture, osteogenic cells or cell aggregates which have migrated into the bone defect and adhered to the particles, in particular to the deformable particles, and to the nondeformable particles, are slowly exposed in a defined manner to stress, i.e., a biomechanical stimulus, in particular when they are located at a distance from the particles for which distraction is effective. As a result of the defined expansion of the deformable particles in the bone defect and the associated motion of the nondeformable particles and the resulting distraction of cells adhered to the particles, a three-dimensional callus distraction is achieved. In this manner a callus precursor is produced in the entire defect all at once by distraction, and then only needs to ossify. This stimulus is advantageously achieved in essentially a large number of cells, particularly preferably in all cells at the same time. According to the invention, biomechanical stimuli may be transmitted directly to the osteoblasts without the need for fibroblasts. Thus, the distraction may act on the osteoblasts with comparatively small forces. Without being bound to theoretical aspects, the distraction pulses are transmitted to most of the osteoblasts via the nondeformable particles, in particular when more nondeformable particles than deformable particles are present in the granulate mixture, and/or when the nondeformable particles are larger than the deformable particles.

The granulate mixture according to the invention may advantageously be used in methods, preferably methods according to the invention, for bone regeneration, in particular for three-dimensional callus distraction.

According to the invention, the granulate mixture according to the invention preferably transmits biomechanical pulses, in particular expansion stimuli or pressure stimuli, to the cells surrounding the granulate mixture, so that the cells may be distracted or compressed by distances of at least 0.5 µm in particular 1 µm more preferably 2 µm, most preferably 10 µm to preferably 100 µm, very particularly preferably 1000 µm, more particularly preferably 1 cm, most particularly preferably up to 10 cm. Thus, according to the invention the granulate mixture according to the invention preferably changes in length and/or width of the deformable particles by the above-referenced preferred distances. Biomechanical pulses are transmitted to the surrounding cells by virtue of this preferred change in length and/or width of the deformable particles. For example, cells which adhere to the particles at at least two adhesion points are expanded by the change in dimension. However, cells surrounding the particles may also experience a pressure pulse as a result of the change in dimension of the particles. The pulses may also be transferred via the body's own fibrin network. However, in particular the pulses are relayed to the cells also via the nondeformable particles, since the nondeformable particles which surround the deformable particles in the granulate mixture are likewise moved by the deformation of the deformable particles.

Thus, the deformation of the deformable particles not only causes a pulse relay to osteoblasts, but also moves the nondeformable particles surrounding the deformable particles, so that the nondeformable particles may likewise relay pulses to the osteoblasts as a result of the motion. The nondeformable particles are thus able to enlarge the surface for adhesion of the osteoblasts and for transmitting the pulses, which normally are formed only by the deformable particles, to the osteoblasts. This may result in a cost reduction, for example, in particular when the deformable particles are more expensive to manufacture than the nondeformable particles.

The pulses may also surprisingly and advantageously be controlled by the size or the size mixtures of the deformable particles and/or of the nondeformable particles, for example controlled in their intensity, duration, and/or speed.

The pulses may also surprisingly and advantageously be controlled by the mixing ratio of the deformable particles to the nondeformable particles, for example controlled in their intensity, duration, and/or speed.

Thus, one skilled in the art is able to select the composition of the particles in a granulate mixture according to the invention in such a way that the relay of pulses to the cells occurs with regard to the desired parameters, for example with regard to the duration of distraction, the speed of distraction, and/or the intensity of distraction.

One skilled in the art is thus able to influence these parameters very easily, namely, by simply changing the size and/or the mixing ratio of the particles in the granulate mixture. In addition, a granulate mixture according to the invention may be easily and inexpensively prepared. For example, conventional nondeformable particles from the prior art may be mixed with the deformable particles without a high expenditure of effort.

According to the invention, the biomechanical pulses are preferably transmitted at a maximum distraction rate of 1 mm/day. According to the invention, the expansion stimuli are preferably transmitted at a maximum distraction rate of 1 mm/day. According to the invention, the pressure stimuli are preferably transmitted at a maximum distraction rate of 1 mm/day.

According to the invention, the degradation kinetics of the deformable particles are adapted to the time schedule for a distraction to be carried out using the granulate mixture according to the invention.

According to the invention, the material of the deformable particles is preferably expandable, contractible, and/or deformable in a predefined and controlled manner as a function of an external action of force. The material may have plastic or elastic properties. These properties of the material enable the capacity, provided according to the invention, of the deformable particles to reversibly or irreversibly change in volume in a predefined and controlled manner.

According to the invention, the starting volume of the deformable particles preferably changes at a predetermined rate. According to the invention, the maximum rate at which the starting volume of the deformable particles is able to change is great enough that the cells adhering to the particles, i.e., to the deformable particles and/or to the nondeformable particles, and/or the cells surrounding the particles, are distracted and/or compressed a maximum of 1.5 mm/day, particularly preferably 1.2 mm/day, in particular 1 mm/day, most preferably 0.9 mm/day.

In one preferred embodiment, the volume of the deformable particles may change in a predefined and controlled manner at a rate at which expansion or contraction of a volume of $1000 \, \mu m^3$ to $216,000 \, \mu m^3$ occurs at a maximum of 0.6 mm per day in at least one spatial coordinate, particularly preferably a maximum of 0.577 mm per day, in particular a maximum of 0.55 mm per day, most preferably a maximum of 0.5 mm per day. In one preferred embodiment, the volume may change in a predefined and controlled manner at a rate at which expansion or contraction of a volume of 1000 µm³ to 216,000 µm³ occurs in at least one spatial coordinate at a maximum of at least 0.01 mm per day, particularly preferably at least 0.1 mm per day, in particular at least 0.2 mm per day, most preferably at least 0.5 mm per day.

In one preferred embodiment, the volume of the deformable particles may change in a predefined and controlled manner at a rate at which expansion or contraction of a section of the body diagonals of the volume of the swelling agent between 10 µm and 60 µm in length occurs at a maximum of 0.6 mm per day, particularly preferably a maximum of 0.577 mm per day, in particular a maximum of 0.55 mm per day, most preferably a maximum of 0.5 mm per day. In one preferred embodiment, the volume may change in a predefined and controlled manner at a rate at which expansion or contraction of a section of the body diagonals of the volume of the swelling agent between 10 and 60 µm in length occurs at least 0.01 mm per day, particularly preferably at least 0.1 mm per day, in particular at least 0.2 mm per day, most preferably at least 0.5 mm per day.

According to the invention, the deformable particles are preferably designed in such a way that the starting volume of the deformable particles is able to change continuously. According to the invention, the deformable particles are preferably designed in such a way that the starting volume of the deformable particles is able to change discontinuously.

In the context of the present invention, "in a predefined and controlled manner" is understood to mean a change in the starting volume, in particular an expansion or contraction, which occurs over a predetermined distance and/or a predetermined volume, and whose rate, i.e., the expansion rate, contraction rate, or rate of change in volume, is likewise predetermined, i.e., intentionally selected. According to the invention, a change in the volume may also be only a change in the shape of the volume. According to the invention, the point in time of the expansion, contraction, or start of the change in volume may also preferably be predetermined, i.e., intentionally selected.

In the context of the present invention, "expansion" is understood to mean an enlargement of the deformable particles along at least one spatial axis. According to the invention, the enlargement preferably takes place along one spatial axis. According to the invention, the enlargement preferably takes place along two spatial axes. According to the invention, the enlargement preferably takes place along all three spatial axes.

In the context of the present invention, "contraction" is understood to mean a reduction in size of the deformable particles along at least one spatial axis, preferably along one spatial axis, two spatial axes, or all three spatial axes.

According to the invention, at least one deformable particle is mixed with at least one nondeformable particle.

In one embodiment, it may be provided in particular that the at least one nondeformable particle contains a bone replacement material.

In one embodiment, it may be provided in particular that the at least one nonexpandable particle contains a bone replacement material.

In one embodiment, it may be provided in particular that the bone replacement material is an organic or an inorganic bone replacement material.

In one embodiment, it may be provided in particular that the bone replacement material is allogenic or autogenic bone.

In one embodiment, it may be provided in particular that the at least one nondeformable particle contains hydroxyapatite and/or tricalcium phosphate.

In one embodiment, it may be provided in particular that the at least one nonexpandable particle contains hydroxyapatite and/or tricalcium phosphate.

In one embodiment, it may be provided in particular that the at least one nondeformable particle contains hydroxyapatite. In one embodiment, it may be provided in particular that the at least one nondeformable particle contains tricalcium phosphate. In one embodiment, it may be provided in particular that the at least one nondeformable particle is composed of hydroxyapatite. In one embodiment, it may also be provided in particular that the at least one nondeformable particle is composed of tricalcium phosphate.

In one embodiment, it may be provided in particular that the at least one nonexpandable particle contains hydroxyapatite. In one embodiment, it may be provided in particular that the at least one nonexpandable particle contains tricalcium phosphate. In one embodiment, it may be provided in particular that the at least one nonexpandable particle is composed of hydroxyapatite. In one embodiment, it may also be provided in particular that the at least one nonexpandable particle is composed of tricalcium phosphate.

In one embodiment, it may be provided in particular that the plurality of the nondeformable, in particular nonexpandable, particles is composed of the same or of different materials.

In one alternative embodiment according to the invention, the nondeformable particles are porous. In one alternative embodiment according to the invention, the nondeformable particles are nonporous.

According to the invention, the at least one nondeformable particle is preferably produced in vitro.

In one alternative embodiment according to the invention, the nondeformable particles are particles known on the market, such as Bio-Oss® from Geistlich Pharma AG, BONITmatrix® from DOT GmbH, or cycIOS® and Ceros® from Mathys AG.

According to the invention, the at least one nondeformable particle preferably has a particle size of 0.1 µm to 50 mm.

According to the invention, the at least one nonexpandable particle preferably has a particle size of 0.1 µm to 50 mm.

In one embodiment according to the invention, the at least one nondeformable particle has a particle size of 1 µm to 50 mm.

In one embodiment according to the invention, the at least one nonexpandable particle has a particle size of 1 µm to 50 mm.

In one embodiment according to the invention, the at least one nondeformable particle has a particle size of 0.01 mm to 10 mm.

In one embodiment according to the invention, the at least one nonexpandable particle has a particle size of 0.01 mm to 10 mm.

In one embodiment according to the invention, the at least one nondeformable particle has a particle size of 0.1 mm to 10 mm.

In one embodiment according to the invention, the at least one nonexpandable particle has a particle size of 0.1 mm to 10 mm.

In one embodiment according to the invention, the particle size is 0.2 mm to 5 mm. In one embodiment according to the invention, the particle size is 0.5 mm to 5 mm. In one embodiment according to the invention, the particle size is 0.6 mm to 5 mm. In one embodiment according to the invention, the particle size is 0.5 mm to 4 mm.

In one embodiment according to the invention, the particle size is at least 0.1 mm. In one embodiment according to the invention, the particle size is at least 0.2 mm. In one embodiment according to the invention, the particle size is at least 0.3 mm. In one embodiment according to the invention, the particle size is at least 0.4 mm. In one embodiment according to the invention, the particle size is at least 0.5 mm. In one embodiment according to the invention, the particle size is at least 0.6 mm.

In one embodiment according to the invention, the maximum particle size is 10 mm. In one embodiment according to the invention, the maximum particle size is 5 mm. In one embodiment according to the invention, the maximum particle size is 4 mm. In one embodiment according to the invention, the maximum particle size is 2 mm. In one embodiment according to the invention, the maximum particle size is 1 mm.

In one alternative embodiment, it may be provided in particular that the particles of the plurality of nondeformable, in particular nonexpandable, particles are present in a single particle size.

However, in one alternative embodiment it may also be provided that the particles of the plurality of nondeformable, in particular nonexpandable, particles are present in at least two different particle sizes. In one alternative embodiment, it may also be provided in particular that the particles of the plurality of nondeformable, in particular nonexpandable, particles are present in two different particle sizes. In one alternative embodiment, it may also be provided in particular that the particles of the plurality of nondeformable, in particular nonexpandable, particles are present in three different particle sizes. In one alternative embodiment, it may also be provided in particular that the particles of the plurality of nondeformable, in particular nonexpandable, particles are present in four different particle sizes. In one alternative embodiment, it may also be provided in particular that the particles of the plurality of nondeformable, in particular nonexpandable, particles are present in five different particle sizes.

In one alternative embodiment, it may also be provided in particular that the particles of the plurality of nondeformable, in particular nonexpandable, particles of the granulate mixture are present in one to ten, in particular one to five, or also in two to ten, in particular two to five, different particle sizes.

In one alternative embodiment, it may also be provided in particular that the particles of the plurality of nondeformable, in particular nonexpandable, particles of the granulate mixture are present in a plurality of different particle sizes.

In one alternative embodiment according to the invention, the nondeformable particles in the granulate mixture are larger than the deformable particles. In one alternative embodiment according to the invention, the nondeformable particles in the granulate mixture are up to 10 times larger, in particular up to 100 times larger, than the deformable particles.

According to the invention, the at least one nondeformable particle is preferably nonexpandable or noncontractible and/or is not able to change its shape in some other way, for example by changing the surface contour. According to the invention, the at least one nondeformable particle is preferably nonexpandable and/or noncontractible. According to the invention, the at least one nondeformable particle is preferably nonexpandable and noncontractible.

According to the invention, the at least one nondeformable particle is preferably nonexpandable.

According to the invention, the nondeformable particles are preferably nonexpandable and noncontractible particles.

According to the invention, the nondeformable particles are preferably inflexible particles. According to the invention, preferably no change in volume occurs for the nondeformable particles, for example when the particles contact a liquid.

According to the invention, the granulate mixture, in particular before its use, is not embedded in a nonexpandable polymer matrix, in particular in a matrix.

In one alternative embodiment according to the invention, in addition to the deformable and nondeformable particles the granulate mixture contains cells, for example stem cells.

In one alternative embodiment according to the invention, in addition to the deformable and nondeformable particles the granulate mixture contains growth factors. The growth factors may be bound to the particles, for example either to the deformable particles and/or to the nondeformable particles. However, the growth factors may also not be bound to the particles.

The present invention further relates to a method for producing a granulate mixture according to the invention, wherein at least one deformable, in particular expandable, particle, in particular a plurality of deformable, in particular expandable, particles, and at least one nondeformable, in particular nonexpandable, particle, in particular a plurality of nondeformable, in particular nonexpandable, particles, are mixed.

The present invention further relates to a method for regenerating a bone, wherein at least one granulate mixture according to the invention is introduced into a defect region of a bone.

The present invention further relates to medical procedures in which a granulate mixture according to the invention is used.

The invention thus further relates to the first medical indication of a granulate mixture of deformable, in particular expandable, particles and nondeformable, in particular nonexpandable, particles, in particular of a granulate mixture according to the invention.

In one embodiment according to the invention, the granulate mixture is introduced into a defect region of a bone in such a way that the at least one deformable, in particular expandable, particle comes into contact with a liquid.

In one embodiment according to the invention, the bone defect is revivified before the granulate mixture is introduced.

Accordingly, within the scope of the method according to the invention for bone regeneration, in one preferred embodiment a granulate mixture composed of deformable and nondeformable particles, in particular a granulate mixture according to the invention, is introduced into a defect region of a bone. In this defect region the granulate mixture is enclosed by a blood clot; i.e., the surfaces of the particles contact the autologous cells contained in the blood clot. After the granulate mixture has been introduced into the defect region of a bone, a change in volume, i.e., in particular a decrease or increase in volume, of the deformable particles is induced as the result of a liquid. This results in expansion and/or change in shape, and thus, the desired biomechanical stimulation of the osteogenic cells attached to the deformable particles and the nondeformable particles, and thus results in distraction and therefore bone regeneration. According to the invention, the action of force preferably occurs within the body, in particular within the bone defect.

According to the invention, the change in volume of the deformable particles may lie in various ranges. The volume change is preferably approximately 10% of the longitudinal expansion of the cells or cell groups adhering to the deformable particles.

According to the invention, the change in the expansion distance is preferably at least 0.5 µm, particularly preferably at least 1 µm, more preferably at least 10 µm, even more preferably at least 100 µm, very preferably at least 1000 µm, very particularly preferably at least 10 mm, and most preferably at least 100 mm.

According to the invention, the change in the expansion distance is preferably 100 mm maximum, particularly preferably 10 mm maximum, more preferably 1000 µm maximum, even more preferably at least 100 µm maximum, very preferably 10 µm maximum, very particularly preferably 1 maximum, and most preferably 0.5 µm maximum.

According to the invention the distraction distance is preferably 5 mm to 10 mm.

According to the invention, the distraction force of the deformable particles must preferably be greater than the contraction force of the fibrin framework or of the blood clot.

According to the invention, the distraction resulting from the deformation, expansion, or contraction of the deformable particles preferably begins one day after the granulate mixture is introduced into the bone defect. According to the invention, the distraction resulting from the deformation, expansion, or contraction of the deformable particles preferably begins one week after the granulate mixture is introduced into the bone defect. The beginning of the distraction may be specified by a casing of the deformable particles, in particular by the thickness of the casing.

In one embodiment according to the invention, the distraction takes place over a period of several days or weeks. In one embodiment according to the invention, the distraction takes place over a period of several days. In one embodiment according to the invention, the distraction takes place over a period of several weeks.

In one embodiment according to the invention, the distraction takes place over a period of at least one day, in particular at least 2 days, and a maximum of 300 days, in particular a maximum of 100 days.

In one embodiment according to the invention, the distraction takes place over a period of at least one day. In one embodiment according to the invention, the distraction takes place over a period of at least 2 days. In one embodiment according to the invention, the distraction takes place over a period of at least 5 days. In one embodiment according to the invention, the distraction takes place over a period of at least 10 days.

In one embodiment according to the invention, the distraction takes place over a maximum period of 300 days. In one embodiment according to the invention, the distraction takes place over a maximum period of 100 days. In one embodiment according to the invention, the distraction takes place over a maximum period of 50 days.

In one embodiment according to the invention, the distraction takes place over a period of several days, in particular over a period of 5 to 20 days, particularly preferably over a period of approximately 10 days, in particular 10 days.

According to the invention, the rate of change of the volume is at least great enough that cells adhering to the particles are distracted at least 1 µm/day. According to the invention, the maximum rate of change of the volume is great enough that cells adhering to the particles are distracted between 0.5 mm/day and 1 mm/day. According to the invention, the maximum rate of change of the volume is great enough that cells or osteogenic, callus-producing tissue adhering to the particles are distracted a maximum of 1 mm/day. A more rapid distraction rate than 1 mm/day results in differentiation of connective tissue instead of bone. As a result of the change in volume, the deformable particles transmit to the cells contained in the blood clot and adhered to the deformable and nondeformable particles biomechanical stimuli which trigger the body's own regenerative forces, thereby forming new autologous bone material. This new bone material does not differ from the original bone material surrounding the defect. The change in volume of the deformable particles results in biomechanical stimulus transmission throughout the entire space occupied by the granulate mixture, so that a biomechanical stimulus is transmitted to a much larger number of cells than for distraction osteogenesis from the prior art. According to the invention, the biomechanical stimulus is preferably transmitted from the deformable particles directly to osteoblasts, as well as by the nondeformable particles to the osteoblasts.

In one embodiment according to the invention, the distraction takes place in all three spatial directions. In one alternative embodiment according to the invention, the distraction takes place directed in one or two spatial directions. In one alternative embodiment according to the invention, the distraction takes place directed in one spatial direction. Without being bound to theoretical aspects, in some situations it may be advantageous to have the distraction take place directed in one spatial direction so that the distraction follows a possible orientation of the fibers.

For a distraction according to the invention, the biomechanical stimuli according to the invention may preferably be transmitted not only directly to osteoblasts adhering to the particles, but also indirectly via fibroblasts. According to the invention, fibroblasts adhering to the particles preferably further transmit the distraction stimulus to osteoblasts in a metered manner. Without being bound to theoretical aspects, after completion of the distraction the fibroblasts in the so-called "null zone" also become osteoblasts and likewise form bone. For a decreasing distraction rate, the number of fibroblasts preceding the osteoblasts changes.

In contrast, distraction osteogenesis from the prior art transmits biomechanical stimuli via a two-dimensional interface composed of bone or another material only to cells which directly contact this two-dimensional interface.

Without being bound to theoretical aspects, cell distraction as well as tissue distraction may be achieved by the method according to the invention.

In conjunction with the present invention, cell distraction is understood to mean the distraction of individual cells, in particular osteoblasts. These individual cells attach to the deformable or nondeformable particles, and experience direct or indirect distraction pulses as a result of the deformation of the deformable particles. In one embodiment according to the invention, a distraction pulse experienced by a cell, in particular an osteoblast, is 1 µm to 10 µm. In one embodiment according to the invention, the distraction distance a cell, in particular an osteoblast, is pulled is 1 µm to 200 µm. In one embodiment according to the invention, the distraction distance a cell, in particular an osteoblast, is pulled is at least 1 µm to a maximum of 10 µm. In one embodiment according to the invention, the distraction distance a cell, in particular an osteoblast, is pulled is at least 10 µm to a maximum of 200 µm.

In one embodiment according to the invention, the rate at which a cell, in particular an osteoblast, is pulled is at least 1 µm/day.

In conjunction with the present invention, tissue distraction is understood to mean the distraction of a tissue, for example a bone tissue, in particular a callus. The tissue is thus composed of a plurality of cells, in particular also osteoblasts. The tissue, in particular a callus, attaches to the deformable or nondeformable particles and experiences direct or indirect distraction pulses as a result of the deformation of the deformable particles. In one embodiment according to the invention, a distraction pulse experienced by a tissue, in particular a callus, is 1 µm to 1000 µm. In one embodiment according to the invention, the distraction distance a tissue, in particular a callus, is pulled is 10 µm to 30 cm. In one embodiment according to the invention, the distraction distance a tissue, in particular a callus, is pulled is 10 µm to 3 cm. In one embodiment according to the invention, the distraction distance a tissue, in particular a callus, is pulled is 10 µm to 10 mm. In one embodiment according to the invention, the distraction distance a tissue, in particular a callus, is pulled is at least 0.2 mm to a maximum of 5 mm.

In one embodiment according to the invention, the distraction distance a tissue, in particular a callus, is pulled is at least 10 µm. In one embodiment according to the invention, the distraction distance a tissue, in particular a callus, is pulled is at least 100 µm. In one embodiment according to the invention, the distraction distance a tissue, in particular a callus, is pulled is at least 1 mm. In one embodiment according to the invention, the distraction distance a tissue, in particular a callus, is pulled is 30 cm maximum. In one embodiment according to the invention, the distraction distance a tissue, in particular a callus, is pulled is 10 cm maximum. In one embodiment according to the invention, the distraction distance a tissue, in particular a callus, is pulled is 3 cm maximum. In one embodiment according to the invention, the distraction distance a tissue, in particular a callus, is pulled is 1 cm maximum. In one embodiment according to the invention, the distraction distance a tissue, in particular a callus, is pulled is 0.5 cm maximum.

In one embodiment according to the invention, the rate at which a tissue, in particular a callus, is pulled is at least 10 µm/day. In one embodiment according to the invention, the rate at which a tissue, in particular a callus, is pulled is at least 0.1 mm/day. In one embodiment according to the invention, the rate at which a tissue, in particular a callus, is pulled is at least 0.25 mm/day. In one embodiment according to the invention, the rate at which a tissue, in particular a callus, is pulled is 2 mm/day maximum. In one embodiment according to the invention, the rate at which a tissue, in particular a callus, is pulled is approximately 1 mm/day.

In one embodiment according to the invention, the rate at which a tissue, in particular a callus, is pulled is at least 0.25 mm/day and a maximum of 2 mm/day. In one embodiment according to the invention, the rate at which a tissue, in particular a callus, is pulled is at least 0.5 mm/day and a maximum of 2 mm/day. In one embodiment according to the invention, the rate at which a tissue, in particular a callus, is pulled is at least 0.5 mm/day and a maximum of 1.5 mm/day.

Thus, the invention provides a method in which a granulate mixture composed of deformable particles and nondeformable particles is introduced into a bone defect, and the deformable particles in the bone defect change in volume and/or shape. As a result of the change in volume and/or shape, biomechanical stimuli are transmitted to cells, in particular osteoblasts, present on the outer surfaces of the deformable particles and the nondeformable particles, thereby stimulating the cells to form bone. The device thus transmits biomechanical stimuli for utilization of the body's own regenerative forces.

The method according to the invention is therefore a three-dimensional distraction. In the context of the present invention, "three-dimensional distraction" is understood to mean distractive bone regeneration in which biomechanical stimuli are transmitted to a bone fragment not only at the interface, i.e., in two dimensions, but also throughout a given volume, i.e., in three dimensions.

According to the invention it may preferably be provided that the distraction occurs along one spatial axis. This may be achieved, for example, by using an alternative embodiment of the deformable particles in which the length of the particles is changed by a bellows, for example.

The method according to the invention uses the body's own healing mechanisms as a bioreactor. Thus, the bone formation occurs under natural conditions, so that the necessary aspects such as growth factors, hormones, and cell composition are implicitly taken into account. In this manner the method according to the invention overcomes problems which may arise as a result of the highly complex control for bone regeneration, as well as the problems of a slow and complicated bone regeneration process using distraction methods from the prior art.

According to the invention, the bone defect is preferably revivified before the device according to the invention is introduced. According to the invention, in the method according to the invention before the device according to the invention is introduced into a bone defect this defect is preferably surgically revivified, and in particular bleeding is induced. A blood clot forms in the defect as a result of the surgical revivification and the induced bleeding.

After the surgical revivification of the bone defect, according to the invention a granulate mixture according to the invention is preferably introduced into the bone defect. The particles are enclosed, in particular completely enclosed, by the blood clot which forms. The deformable particles, for example also the swelling agent forming the particles, preferably come into contact with a liquid, for example the blood in the blood clot.

According to the invention, the granulate mixture is introduced into a defect region of a bone in such a way that the swelling agent of the deformable particles comes into contact with a liquid.

According to the invention, the deformable particles thus preferably change in volume after a defined point in time. According to the invention, the deformable particles preferably change in volume after one day. According to the invention, the deformable particles preferably change in volume after one week. Without being bound to theoretical aspects, the blood clot does not contract, but instead enlarges corresponding to the increase in volume of the deformable particles. The cells activated by the granulate mixture may be converted to proliferating osteoblasts which produce the extracellular matrix, and a callus may be formed which subsequently ossifies. When the deformable particles according to the invention are preferably biodegradable, the deformable particles are subsequently absorbed and/or metabolized. Thus, the bone defect may be filled with bone tissue which according to the invention is preferably produced by the described biomechanical stimuli from the granulate mixture. According to the invention, growth factors and other substances besides the granulate mixture may preferably be dispensed with. According to the invention, the newly formed bone material preferably differs, if at all, only slightly, either histologically or in its biological or medical value, from the original bone which surrounds it.

According to the invention, the absorption time of the deformable particles is approximately 1 to 2 years, particularly preferably approximately 1.5 years, in particular 1.5 years.

Since the deformable particles according to the invention are preferably biodegradable, the space resulting from the degradation of the device may be used for the extracellular matrix. According to the invention, the degradation of the deformable particles may preferably be adjusted in such a way that after a few weeks the particles degrade after they have emitted the biomechanical stimuli, and the resulting space is occupied by the extracellular matrix.

In one alternative according to the invention, within the scope of the method according to the invention particles are used whose sheathing has cell adhesive properties. The surface of the sheathing particularly preferably has cell adhesive properties. The surface of the sheathing plays a role in the growth of cells from the blood clot. An adhesion of the cells to the sheathing preferred according to the invention may be influenced by virtue of the surface chemistry, surface physics, and surface topography of the sheathing. According to the invention the surface of the sheathing is preferably hydrophilic. For the ingrowing cells, the interaction between the negatively charged cell membrane and the electrical properties of the surface of the sheathing is preferred according to the invention.

The present invention further relates to the use of a granulate mixture according to the invention for regenerating a bone, wherein the granulate mixture is introduced into a defect region of a bone.

The present invention further relates to the use of deformable, in particular expandable, particles and nondeformable, in particular nonexpandable, particles for producing a granulate mixture, in particular a granulate mixture according to the invention, for regenerating a bone, wherein the granulate mixture is introduced into a defect region of a bone.

The present invention further relates to a granulate mixture containing at least one deformable, in particular expandable, particle and at least one nondeformable, in particular nonexpandable, particle, in particular a granulate mixture according to the invention, for use in the regeneration of a bone.

The invention further relates to the second medical indication of a granulate mixture composed of deformable, in particular expandable, particles and nondeformable, in particular nonexpandable, particles, in particular of a granulate mixture according to the invention, for regenerating a bone, in particular a bone in the jaw region.

The invention further relates to the use of a granulate mixture according to the invention for manufacturing a kit for bone regeneration.

The invention further relates to a kit for bone regeneration, containing a plurality of deformable, in particular expandable, particles and a plurality of nondeformable, in particular nonexpandable, particles. The invention relates in particular to a kit for bone regeneration, containing a granulate mixture according to the invention.

According to the invention, said kits preferably contain at least one surgical instrument, particularly preferably at least one applicator, for example a syringe, and a capsule for absorption of the granulate mixture. According to the invention the kit preferably contains an instruction manual. According to the invention the kit preferably contains a package, particularly preferably a package which allows sterile storage of the granulate mixture.

According to the invention, the components of the kit are associated with the granulate mixture according to the invention.

Further devices such as a surgical instrument, an instruction manual, and/or a package may be associated with the granulate mixture according to the invention.

According to the invention, preferred and alternative embodiments according to the invention of the granulate mixture according to the invention are also understood to be preferred and alternative embodiments according to the invention of uses according to the invention, and as preferred and alternative embodiments according to the invention of a method according to the invention.

According to the invention, preferred and alternative embodiments according to the invention of the methods according to the invention are also understood to be preferred and alternative embodiments according to the invention of the uses according to the invention, and as preferred and alternative embodiments according to the invention of the granulate mixture according to the invention.

FIG. 1 shows a kit 100 which contains an applicator syringe 10 made of sterilizable metal, on the open end 20 of which a disposable capsule 30, made of plastic, for example, is attached. The outwardly facing side of the disposable capsule 30 is provided with a protective cap 40. The disposable capsule 30 contains a granulate mixture 50 according to the invention composed of deformable particles and nondeformable particles. The granulate mixture is injected via the syringe into a bone defect (not illustrated), for example in the jaw region.

The kit 100 according to the invention is used to inject the granulate mixture 50 into a bone defect. After introduction into the bone defect, as a result of the structure and composition according to the invention of the deformable particles, and due to contact with liquid, the volume of the swelling material of the deformable particles changes, resulting in expansion, contraction, and/or change in shape of the deformable particles. The nondeformable particles and the bone cells which in the meantime have become attached to the deformable particles and nondeformable particles are thus distracted for regeneration of the bone.

Figure 2A:
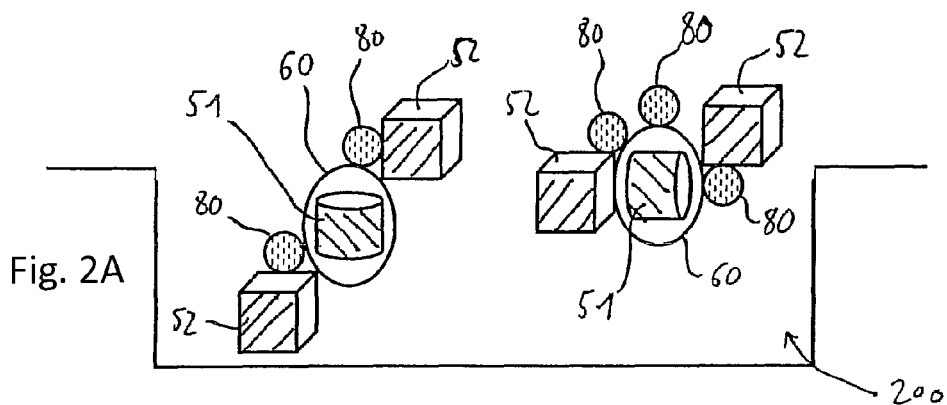
FIG. 2A illustrates a granulate mixture according to the present teachings immediately after introduction into a bone defect.
Figure 2B:
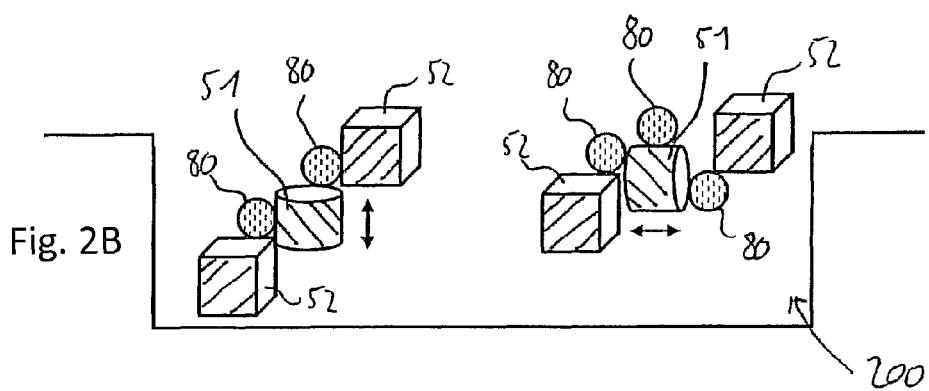
FIG. 2B is a view similar to FIG. 2A illustrating the granulate mixture of the present teachings after the casings of the granulate mixture have degraded.
Figure 2C:
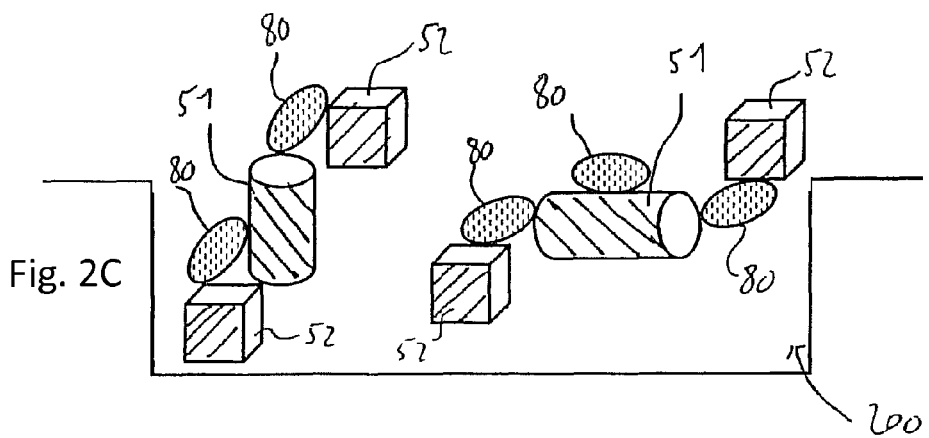
FIG. 2C is another view similar to FIG. 2A showing a change in volume of the deformable particles.

FIG. 2A shows two deformable particles 51 and multiple nondeformable particles 52 of a granulate mixture 50 in a bone defect 200, specifically, immediately after the granulate mixture 50 has been introduced into the bone defect 200, for example by use of a kit 100. The deformable particles 51 are surrounded by casings 60. The deformable particles may be composed of a swelling agent, for example. After being introduced into the defect 200, the casing, which may be made of gelatin, for example, is biologically decomposed and degraded. FIG. 2B shows the situation after the casings 60 have degraded. The deformable particles 51 then come into direct contact with the liquid, in particular blood, present in the bone defect, thus causing the volume of the deformable particles 51 to become enlarged in the longitudinal axis, as schematically illustrated by the double arrows in FIG. 2B. This change in volume of the deformable particles 51 results in expanded particles 51, as is apparent from FIG. 2C. The expansion causes the surrounding nondeformable particles 52 to be pushed away, resulting in distraction of the cells 80 which have attached and adhered to the deformable particles and nondeformable particles 51/52.

Further advantageous embodiments of the invention result from the subclaims. The invention is explained in greater detail with reference to the following exemplary embodiment and the accompanying figures.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A granulate mixture suitable for regenerating a bone comprising a plurality of nondeformable particles and a plurality of expandable particles;
wherein the nondeformable particles of the plurality of nondeformable particles have a particle size of 0.01 mm to 10 mm.

2. The granulate mixture according to claim 1, wherein a mixing ratio of the plurality of expandable particles to the plurality of nondeformable particles in the granulate mixture is 1:99 to 99:1, relative to a number of particles.

3. The granulate mixture according to claim 1, wherein the plurality of expandable particles is composed of a swelling agent.

4. The granulate mixture according to claim 3, wherein the swelling agent is a hydrogel.

5. The granulate mixture according to claim 3, wherein the swelling agent expands as a result of absorption of a liquid selected from a group consisting of: a liquid containing biomolecules, cells, and a combination thereof.

6. The granulate mixture according to claim 5, wherein the liquid is blood.

7. The granulate mixture according to claim 3, wherein the swelling agent for the plurality of expandable particles is composed of a polysaccharide.

8. The granulate mixture according to claim 3, wherein the swelling agent for the plurality of expandable particles is composed of a glucosamine.

9. The granulate mixture according to claim 1, wherein the expandable particles of the plurality of expandable particles have a particle size of 0.0001 mm to 10 mm.

10. The granulate mixture according to claim 1, wherein the expandable particles of the plurality of expandable particles have a particle size of 0.1 mm to 10 mm.

11. The granulate mixture according to claim 1, wherein the expandable particles of the plurality of expandable particles are present in at least two different particle sizes.

12. The granulate mixture according to claim 1, wherein the plurality of nondeformable particles contains a bone replacement material.

13. The granulate mixture according to claim 1, wherein the plurality of nondeformable particles contains hydroxyapatite and/or tricalcium phosphate.

14. The granulate mixture according to claim 1, wherein the nondeformable particles of the plurality of nondeformable particles have a particle size of 0.1 mm to 10 mm.

15. A granulate mixture suitable for regenerating a bone comprising:
a plurality of nondeformable particles; and
a plurality of expandable particles having a swelling agent, wherein the swelling agent expands as a result of absorption of a liquid selected from a group consisting of: a liquid containing biomolecules, cells, and a combination thereof;
wherein a mixing ratio of the plurality of expandable particles to the plurality of nondeformable particles in the granulate mixture is 1:99 to 99:1, relative to a number of particles;
wherein the expandable particles of the plurality of expandable particles have a article size of 0.0001 mm to 10 mm, and further wherein the nondeformable particles of the plurality of nondeformable particles have a particle size of 0.01 to 10 mm.

16. The granulate mixture according to claim 15, wherein the swelling agent is selected from a group consisting of a polysaccharide and a glucosamine.

17. The granulate mixture according to claim 15, wherein the plurality of nondeformable particles contains hydroxyapatite and/or tricalcium phosphate.

18. The granulate mixture according to claim 15, wherein the plurality of nondeformable particles contains a bone replacement material.

19. The granulate mixture according to claim 15, wherein the expandable particles of the plurality of expandable particles are present in at least two different particle sizes.

* * * * *